United States Patent [19]

Weiler

[11] 4,094,875
[45] June 13, 1978

[54] 3-PYRIDYLMETHYL N-(4-CYANOMETHYLPHENYL)CARBAMATE AND DERIVATIVES

[75] Inventor: Ernest D. Weiler, Ambler, Pa.

[73] Assignee: Rohm and Haas Company, Philadelphia, Pa.

[21] Appl. No.: 619,277

[22] Filed: Oct. 3, 1975

Related U.S. Application Data

[62] Division of Ser. No. 475,709, Jun. 3, 1974, Pat. No. 3,929,810.

[51] Int. Cl.$^2$ ............ C07F 3/06; C07F 3/04; C07F 3/14; C07F 1/10

[52] U.S. Cl. ............ 260/270 PY; 260/294.9; 424/245

[58] Field of Search ............ 260/270 PY, 294.9

[56] References Cited

U.S. PATENT DOCUMENTS

| | | | |
|---|---|---|---|
| 3,731,202 | 1/1976 | Ware et al. | 260/294.9 |
| 3,925,397 | 12/1975 | Kilbourn et al. | 260/294.9 |
| 3,929,808 | 12/1975 | Kilbourn et al. | 260/270 PY |

Primary Examiner—Donald G. Daus
Assistant Examiner—Mark L. Berch

[57] ABSTRACT

3-Pyridylmethyl N-(4-cyanomethylphenyl)carbamate and its acid salts and metal salt complexes useful as rodenticides.

2 Claims, No Drawings

3-PYRIDYLMETHYL N-(4-CYANOMETHYLPHENYL)CARBAMATE AND DERIVATIVES

This is a division of application Ser. No. 475,709 filed June 3, 1974, now U.S. Pat. No. 3,929,810.

The present invention relates to 3-pyridylmethyl N-(4-cyanomethylphenyl)carbamate and its acid addition salts and metal salt complexes. The novel compounds are particularly useful, especially in compositions and formulations containing them, for the control and extermination of pest rodents.

The common rat, *Rattus norvegicus,* is vicious and constantly poses a serious threat to the health and well being of man. Rats and mice are destructive animals and a serious nuisance, causing millions of dollars damage annually to farms, agronomic crops, homes, food processing plants and many other businesses. Rats bite at least 14,000 (possibly up to 60,000) people every year, according to the U.S. Public Health Service, and are known carriers of over 35 contagious diseases including bubonic plague, trichinosis, typhus, rat bite fever, amoebic dysentery, tuberculosis, infectious jaundice and rabies. During the years from 1898 to 1923, almost 11 million deaths were caused by rat-borne plagues.

Use of rodenticides, fumigants, sprays and traps are the primary methods employed for the control of pest rodents. The term "pest rodents" refers not only to members of the order Rodentia but also to those of lagomorpha, which cause health hazards or economic loss unless kept in check. Rodenticides may be used in the form of a tracking powder or a bait or may be applied as a spray on the rodent's natural foodstuffs. The rodenticides used as a bait are of two classes: single and multi-dose. Multi-dose rodenticides are usually selected over single-dose rodenticides, as they have been safer in the past than the available single-dose rodenticides. The multi-dose rodenticides are anti-coagulants, including a number of different 4-hydroxy-coumarin and 1,3-indandione compounds. These multi-dose rodenticides consumed in small daily amounts have a lethal effect on rats and mice after liver stores of vitamin K have been depleted. Anti-coagulants are less effective on mice than rats, as mice are considered to be nibblers and may not consume an adequate amount of treated bait to have a lethal effect. A single-dose rodenticide which would be relatively safe to the person handling the material and to non-target species of animals and yet effective on a variety of pest rodents is highly desirable.

Many compounds are toxic to rodents. However, very few of these compounds are anywhere near suitable for use as a rodenticide because it is necessary for the pest rodent to consume voluntarily a sufficient amount of the poison even though sufficient untreated food may also be available. In bait rodenticides, feed acceptance is the key to excellence, and in all rodenticides safety and efficacy are highly important.

3-Pyridylmethyl N-(4-cyanomethylphenyl)carbamate and its derivatives of the present invention are so highly toxic to a wide variety of pest rodents that a single dose is sufficient; yet they are relatively safe for use in the presence of other species which may inadvertently ingest limited quantities of the rodenticide. Furthermore, rats and other pest rodents willingly consume the conpounds in sufficiently lethal amounts when present in baits. Alternatively the compounds may be employed in compositions to be sprayed on natural foodstuffs. They may also be employed in a tracking powder, especially for use against mice, which habitually clean their paws by licking.

3-Pyridylmethyl N-(4cyanophenyl)carbamate and closely related carbamates are known rodenticides, e.g., see Belgium Pat. No. 796,753. The structure requirements, however, for excellent rodenticidal activity in the class of 3-pyridylmethyl N-(4-substituted-phenyl)-carbamates is quite exacting and unpredictable. The only compound now known in this class of carbamates which possesses the stringent requirements and activity for a single-dose rodenticide and wherein the said 4-substituent is a —CH$_2$X group is where X is —CN.

3-Pyridylmethyl N-(4-cyanomethylphenyl)carbamate is readily prepared by the reaction of 3-pyridyl carbinol, a product of commerce, with 4-cyanomethylphenyl isocyanate, preferably in the presence of an inert solvent such as an aromatic hydrocarbon or acetonitrile, in accordance with the following equation:

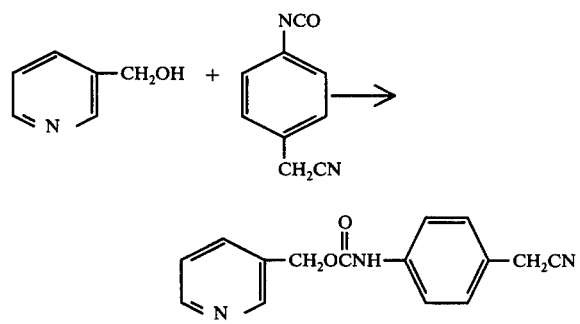

The intermediate 4-cyanomethylphenyl isocyanate is a novel compound. It was made by the reaction of 0.1 mole of phosgene as a 12.5% solution in benzene with 0.05 mole of p-aminobenzyl cyanide in 50 ml. of benzene at 0° to −5° C. for 2 hrs., at room temperature for 3 days, then at reflux temperature for 7 hrs. The reaction mixture was filtered and the filtrate concentrated in vacuo to give 7.5 g. of an oil. The oil was identified by means of its infrared spectrum and was a 95% yield of 4-cyanomethylphenyl isocyanate.

Also included in the compounds of this invention are the acid addition salts and metal salt complexes of 3-pyridylmethyl N-(4-cyanomethylphenyl)carbamate. These also are excellent rodenticides.

The 3-pyridylemthyl N-(4-cyanomethylphenyl)carbamate can form novel acid salts with a strong inorganic or organic acid. Typical strong acids include hydrobromic, hydrochloric, hydrofluoric, nitric, phosphoric, sulfuric, chloroacetic, oxalic, maleic, succinic and p-toluenesulfonic.

The novel metal salt complexes may be depicted by the structure

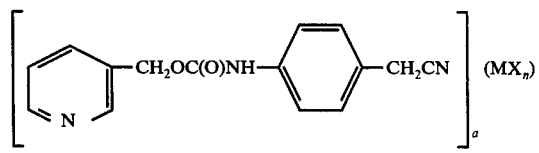

wherein M is a cation of a metal such as cadmium, calcium, cobaltous, cupric, ferrous, ferric, manganous, mercuric, nickel, silver, stannous and zinc; X is an anion forming a salt with the cation M in which the salt has sufficient solubility to form a complex with the compound of the invention such as bromide, chloride, iodide, perchlorate, carbonate, bicarbonate, nitrate, phosphate, sulfate, bisulfate, acetate, maleate, oxalate and p-toluene-sulfonate; $a$ is an integer corresponding to the valence of cation M and $n$ is an integer which for the anion X satisfies the valence of the cation M. The complex with zinc chloride is preferred, but the other complexes are readily made and are useful as equivalents.

The following examples are typical of methods of preparing the novel compounds of this invention.

EXAMPLE 1

Preparation of 3-pyridylmethyl N-(4-cyanomethylphenyl)carbamate

To a solution of p-cyanomethylphenyl isocyanate (3.75 g., 0.0237 mole) in 100 ml. of benzene was added 3-pyridyl carbinol (2.59 g., 0.0237 mole). An exothermic reaction occurred and a precipitate formed. The reaction mixture was heated to reflux then allowed to stand at ambient temperatures for 3 hrs. The solid was filtered off and dried to give 5.8 g. melting at 157°–161.5° C. The product is a 92% yield of 3-pyridylmethyl N-(4-cyanomethylphenyl)carbamate. Recrystallization from methanol gave a solid melting at 162°–163.5° C.

EXAMPLE 2

Preparation of 3-pyridylmethyl N-(4-cyanomethylphenyl)carbamate hydrochloride

To a solution of 3-pyridylmethyl N-(4-cyanomethylphenyl)carbamate (5 g., 0.0187 mole) in 300 ml. of acetone was added an excess of hydrogen chloride in a steady stream. A white suspension formed and was filtered off to give 5.3 g. of solid melting at 215°–216° C. This was a 93.5% yield of 3-pyridylmethyl N-(4-cyanomethylphenyl)carbamate hydrochloride.

EXAMPLE 3

Preparation of the oxalic acid salt of 3-pyridylmethyl N-(4-cyanomethylphenyl)carbamate When the preparation of Example 2 was repeated using the same amount of 3-pyridylmethyl N-(4-cyanomethylphenyl)carbamate in 400 ml. of methanol and oxalic acid dihydrate (2.36 g., 0.0187 mole) in place of hydrogen chloride, there was obtained 2.43 g. of solid melting with decomposition at 174.5°–177° C. This was a 36% yield of 3-pyridylmethyl N-(4-cyanomethylphenyl)carbamate oxalate.

EXAMPLE 4

Preparation of 3pyridylmethyl N-(4-cyanomethylphenyl)-carbamate zinc chloride complex When the oxalic acid in Example 3 above was replaced with zinc chloride (1.27 g., 0.00935 mole) in 40 ml. of methanol, there was obtained 4.2 g. of solid melting at 136°–141° C. with decomposition. This was a 67.5% yield of 3-pyridylmethyl N-(4cyanomethylphenyl)carbamate zinc chloride complex.

Table I gives analytical data on these examples.

Table I

| Example | Empirical Formula | Analysis[1] | | |
|---|---|---|---|---|
| | | % C | % H | % IV |
| 1 | $C_{15}H_{13}N_3O_2$ | 67.1 | 4.7 | 15.7 |
| | | (67.4) | (4.9) | (15.7) |
| 2 | $C_{15}H_{13}N_3O_2 \cdot HCl$ | 59.2 | 4.6 | 13.7 |
| | | (59.3) | (4.7) | (13.8) |
| 3 | $C_{15}H_{13}N_3O_2 \cdot C_2H_2O_4$ | 57.1 | 4.2 | 11.7 |
| | | (57.1) | (4.2) | (11.8) |
| 4 | $C_{15}H_{13}N_3O_2 \cdot \frac{1}{2} ZnCl_2$ | 53.1 | 4.0 | 12.4 |
| | | (53.7) | (3.9) | (12.5) |

[a] the value in parentheses is that calculated from the empirical formula

The 3-pyridylmethyl N-(4-cyanomethylphenyl)carbamate and its derivatives of the present invention may be formulated into rodenticidal compositions such as baits, tracking powders, and sprays. A bait comprises a semi-moist or dry edible carrier and the toxicant. The dry carrier is generally preferred and may be a combination of natural food products such as whole ground corn, steel cut oats, sugar, molasses, rice, vegetable oil, salt, dehydrated fruit, fish meal, tankage or wheat. When necessary to use in damp locations, the matrix may be a water repellent material such as paraffin wax or an acrylic polymer.

The compounds of the present invention may be incorporated as a toxicant in bait formulations, either alone or in combination with other toxicants. When used as the sole toxicant in baits. the compounds of the present invention may be used in any rodenticidally effective concentration.

Depending on the susceptibility of the rodents to the toxicant and the amount of formulated bait generally consumed, concentrations as low as 0.1% may be employed. A typical bait usually contains between about 0.5 and 1.5% of the toxicant by weight but can contain from 0.1 to 99.5% of the toxicant. Rats, mice and other rodents accept the compounds of the present invention quite well when offered free choice between the untreated basal ration and a bait containing one of the compounds of this invention. An example below describes the formulation of a suitable bait, although wide variations in formulation for different conditions of use are of course expected.

BAIT FORMULATION

A 3-pyridylmethyl N-(4-cyanomethylphenyl)carbamate was blended with the basal ration in a Waring laboratory blender to form 50 grams of a homogeneous premix. The amount of compound utilized was determined by the percentage of active material desired in the feed. The formula for the basal ration is shown below, all percentages being by weight:

| | |
|---|---|
| Crude ground corn | 65% |
| Steel cut oats | 25% |
| Powdered sugar | 5% |
| Corn oil | 5% |

The 50 grams of premix containing the toxicant were then mixed with an additional 450 grams of basal ration. These components were mixed in a Little Ford Lodige mixer for 3 minutes.

Tracking powders, which are particularly effective against mice, may be either a compound of the present invention in finely powdered form or a mixture of the compound with powdered carrier, e.g., talc, sugar, milk powder, Indian corn meal, fish meal, cornstarch, flour, and bentonite, or the like or any combination thereof which tends to induce the animals contaminated with the preparation to lick themselves more thoroughly. In tracking powders, a compound of the present invention may be incorporated in amounts from 100% down to 0.1% by weight with proper formulation. An example below describes the preparation of a suitable tracking powder.

TRACKING POWDER

The active compound is finely pulverized by mortar and pestle to form a 100% active tracking powder. To form a 5% active material, it may be mixed with 10X confectioner's sugar in a 1 to 19 ratio and at other ratios for other levels of active compound.

The compounds were preliminarily evaluated for their ability to kill albino rats (*Rattus norvegicus*) by oral administration to two rats at a dosage of 50 mg./kg. In the standard test the effect on the rats is observed over a 14 day period. Table II, Part A, gives the results with typical examples of this invention.

One of the most significant secondary test is a standard one known as the paired-preference test. In this test the rodents are given a free choice between the treated and untreated bait in individual cages or in a communal tank. Such a test most nearly approximates practical use conditions.

When caged individually, they were provided with dual feed cups and separate water devices. When caged in a communal tank, they were offered a multiplicity of feed cups and water devices. The basal ration was offered in excess of daily feed requirements in each of two feeders; one treated with the test compound and one without. For each test, equal numbers of each sex were used.

The gross weight of each feed container and its feed were determined daily and returned to the starting weight by addition of complete replacement of the given diet. The position of the bait and the laboratory diet cups in the cage were reversed every 24 hours to counter any feeding position habit of the rat. The test rodents had free choice between treated and untreated feed. Mortalities were recorded daily.

To meet the criteria for a single-dose product, a rodenticide in this initial test must kill 75% of the rats within 8 days, where the poison bait is available for the first 72 hours of this period.

The results of representative paired preference tests with several dosage levels on individually caged rodents are given in Table II, Part B.

Table II
Rodenticidal Data

A. Oral toxicity

| Example | Dosage (mg./kg.) | Mortality No. dead/Total No. |
|---|---|---|
| 1 | 50 | 2/2 (24 hrs.) |
| 2 | 200 | 2/2 (24 hrs.) |
| 3 | 50 | 2/2 (24 hrs.) |
| 4 | 200 | 2/2 (24 hrs.) |

B. Paired Preference Tests

| Ex. | Rodent | Compound in Basal Ration (ppm) | Mortality No. dead/Total No. |
|---|---|---|---|
| 1 | Norway rat (*Rattus norvegicus*) | 10,000 | 3/4 |
|  | Roof rat (*Rattus rattus*) | 20,000 | 3/4 |
|  | Albino rat | 20,000 | 3/4 |

I claim:
1. A metal salt complex of the structure

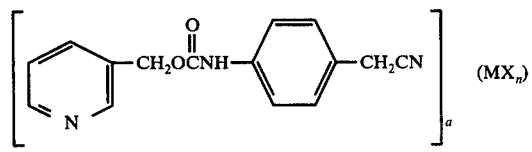

wherein
M is a metal cation of cadmium, calcium, cobaltous, cupric, ferrous, ferric, manganous, mercuric, nickel, silver, stannous or zinc;
X is a bromide, chloride, iodide, perchlorate, carbonate, bicarbonate, nitrate, phosphate, sulfate, bisulfate, acetate, maleate, oxalate, or p-toluene sulfonate anion forming a salt with the cation M in which the salt has sufficient solubility to form a complex with 3-pyridylmethyl N-(4-cyanomethylphenyl)carbamate;
$a$ is an integer corresponding to the valence of cation M; and
$n$ is an integer which for the anion X satisfies the valence of cation M.

2. A complex according to claim 1 wherein M is a zinc cation, X is a chloride anion, $a$ is 2, and $n$ is 2.

* * * * *

UNITED STATES PATENT AND TRADEMARK OFFICE
CERTIFICATE OF CORRECTION

PATENT NO. : 4,094,875

DATED : June 13, 1978

INVENTOR(S) : Ernest D. Weiler

It is certified that error appears in the above-identified patent and that said Letters Patent are hereby corrected as shown below:

Column 1, ln. 66 - delete word "conpounds" and in lieu thereof insert word -- compounds --

Column 2, ln. 48 - delete word "pyridylemthyl" and in lieu thereof insert -- pyridylmethyl --

Column 3, ln. 52 - Example 4 heading insert hyphen (-) between figure "3" and word "pyridylmethyl".

Column 3, ln. 60 - Example 4 - insert hypen (-) between figure "4" and word "cyanomethylphenyl".

Signed and Sealed this

Seventeenth Day of July 1979

[SEAL]

Attest:

LUTRELLE F. PARKER

*Attesting Officer*     *Acting Commissioner of Patents and Trademarks*